US00PP14083P29

(12) United States Plant Patent
Utecht

(10) Patent No.: US PP14,083 P2
(45) Date of Patent: Aug. 19, 2003

(54) GERANIUM PLANT NAMED 'FIP 765'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,584

(22) Filed: Sep. 30, 2002

(51) Int. Cl.[7] ..... A01H 5/00
(52) U.S. Cl. ..... Plt./325

(58) Field of Search ..... Plt./325

*Primary Examiner*—Kent Bell
(74) *Attorney, Agent, or Firm*—Foley & Lardner

(57) ABSTRACT

A new and distinct cultivar of geranium plant named 'Fip 765', characterized by the combined features of lavender colored flowers with white eyes, floriferous with medium sized umbels on brown-red peduncles, dark-green foliage with weak zonation, moderately compact, low, rounded plant habit, and medium to early spring flowering response.

1 Drawing Sheet

Latin name of the genus and species of the plant claimed: *Pelargonium zonale L'Héritier.*
Variety denomination: 'Fip 765'.

BACKGROUND OF THE INVENTION

The present invention comprises a new and distinct cultivar of geranium, botanically known as *Pelargonium zonale,* and hereinafter referred to by the cultivar name 'Fip 765'.

'Fip 765' is a product of a planned breeding program which had the objective of creating new zonal geranium cultivars with violet to lavender flower color in combination with dark-green foliage.

'Fip 765' originated from a hybridization made by the inventor Angelika Utecht in a controlled breeding program in Galdar, Gran Canaria, Spain, in 1996.

The female parent was an unpatented hybrid, No. I95-112-14, having single-type, purple-pink flowers with reddish eyes, dark green foliage, and compact, small plant habit. The male parent of 'Fip 765' was the unpatented commercial variety 'Arlena', (Plant Breeder's Rights grant under the variety denomination 'Penarl'), with light lavender semi-double flowers, uniform green foliage without zonation, and small, compact plant habit.

'Fip 765' was selected as one flowering plant within the progeny of the stated cross by Angelika Utecht in 1997 in a controlled environment in Galdar, Gran Canaria, Spain. The first act of asexual reproduction of 'Fip 765' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fip 765' are firmly fixed and are retained through successive generations of asexual reproduction.

'Fip 765' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

BRIEF SUMMARY OF THE INVENTION

The following traits have been repeatedly observed and are determined to be basic characteristics of 'Fip 765' in combination distinguish this geranium as a new and distinct cultivar:

1. Lavender and white, semi-double flowers;
2. medium to large inflorescences on reddish peduncles;
3. dark green foliage with weak zonation;
4. moderately compact, round plant habit; and
5. early to medium spring flowering response.

Of the many commercial cultivars known to the present inventor, the most similar in comparison to 'Fip 765' is the variety 'Fislypso' (U.S. Plant Pat. No. 11,162), and the cultivar 'Fip 749' (Co-pending U.S. Plant patent application No. 10/259,593).

In comparison to 'Fislypso', 'Fip 765' has a slightly lighter main flower color, deeper reddish colored peduncles, and dark-green foliage, while 'Fislypso' has medium green foliage, and even lower foliage canopy. In comparison to 'Fip 749', 'Fip 765' has a more bluish hue of flower color, longer peduncles, while plant habit, respectively size of foliage canopy, is similar.

BRIEF DESCRIPTION OF THE DRAWING

The accompanying photographic drawing shows typical flower and foliage characteristics of 'Fip 765' with colors being as true as possible with an illustration of this type. The drawing depicts a side elevational view of a typical potted flowering plant of 'Fip 765'.

DETAILED BOTANICAL DESCRIPTION

The measurements were taken in Hillscheid, Germany, in mid May 2002, 10 weeks after planting of rooted cuttings. The plants were growing in 14 cm plastic pots, they had not been pinched.

In the following description color references are made to The Royal Horticultural Society Colour Chart. The color values were determined indoors from plants developed in a green-house in May 2002 in Hillscheid, Germany.

Inflorescence:

*Type.*—Umbel, between umbrella-shape and semi-sphere.

*Average diameter.*—105 mm.

*Average depth.*—60 mm.

*Peduncle length.*—175 mm.

*Peduncle color.*—Mainly reddish-brown, RHS 181 A, near base green, RHS 143 C.

*Pedicel length.*—29 mm.

*Pedicel color.*—Mainly brownish-red, RHS 179 A, near base, RHS 179 B.

*Number of flowers per umbel.*—About 20–30.

Corolla:

*Average diameter.*—Approx. 48 mm.

*Form.*—Semi-double.

*Shape.*—Round to slightly zygomorphic, flat cup-shape.

*Number of petals.*—7–9.

*Number of petaloids.*—1–2.

*Shape of petals.*—Obovate, base acute, upper ends rounded to truncate, margin entire.

*Size of petals.*—Upper petals: 25–27 mm long, 18–20 mm wide; lower petals: 22–24 mm long, 20–22 mm wide.

*Color (general tonality from a distance of three meters).*—Light lavender with white eyes.

*Color of upper petals.*—Main part RHS 78C.

*Markings of upper petals.*—Mainly white bases, RHS 155 D, to RHS 75 D.

*Color of lower petals.*—RHS 78 B.

*Markings of lower petals.*—None.

*Color of lower surface of petals.*—Middle part almost white, RHS 75 D, to lavender, RHS 75 A, near margin.

*Petaloids.*—Same color as petals.

*Color of sepals.*—Outer surface: mainly light green, RHS 143 C, base RHS 179 A; inner surface: light green, RHS 143 C, base RHS 179 B.

*Number of sepals.*—5.

*Shape of sepals.*—Linear to lanceolate, acute tip, truncate base, surface with very short pubescence, margin entire.

*Size of sepals.*—10–12 mm long, 4 mm wide for the largest upper sepal, 2–3 mm in width for the other sepals.

Bud (just prior to petals unfolding):

*Shape.*—Elliptical.

*Color of sepals.*—Light green, RHS 143 B, base weakly reddish, RHS 179 B.

*Color of petals.*—RHS 75 D in the middle part, RHS 74 C near margin.

*Length.*—16 mm.

*Width.*—10 mm.

Reproductive organs:

*Androecium.*—7–9 fertile anthers, moderate pollen, yellow-orange, RHS 30 A, filaments white, RHS 155 D, to very light pink, RHS 68 D.

*Gynoecium.*—One pistil, style and stigma dark pink, RHS 51 A, 5–6-lobed stigma.

*Fertility/seed set.*—Occasionally weak seed set, mainly in late summer to fall.

*Fruit.*—Oblong, about 5–6 mm wide, rostrum (beak) 38–40 mm long.

*Seed.*—Oblong, 4–5 mm long, brown, RHS 177 B.

Spring flowering response period: In Hillscheid, Germany, in 2002 plants had on average 0.7 flowers opened 8 weeks after planting of rooted cuttings.

Outdoor flower production: Continuously and rich flowering, the flower count in 2002 in Hillscheid, Germany, indicated about 5–6 inflorescence per plant in mid May.

Durability: Good stability of flower color, fair rain resistance.

Lastingness of the individual flower: About 5–6 days at 18° C., about 15–17 days for the umbel.

Fragrance: None.

PLANT

Foliage:

*Shape.*—Kidney-shaped, with cordate base and with open gap between the lowest lobes, apex rounded with weak lobes.

*Margin.*—Bi-crenate.

*Texture.*—Upper surface smooth, velvety, dull.

*Size of leaf.*—90 mm wide, 55 mm long.

*Color of upper surface.*—Dark-green, approximately RHS 137 A.

*Color of zonation.*—Brown, about RHS 166 A, weak, may not always be visible on mature leaves during the summer.

*Color of lower surface.*—RHS 137 C.

*Petioles.*—65–75 mm long, 3 mm diameter, light green in color, approximately RHS 143 B.

General appearance and form:

*Stem color.*—Green, RHS 143 A to 143 B.

*Internode length.*—10–15 mm.

*Branching pattern.*—7.3 branches.

*Plant size.*—Height: 17.6 cm, width: 26.2 cm, (10-week-old plants, as described and measured from the top of the soil (base of the main stem) to the surface of the foliage canopy, without inflorescences).

Pest/disease resistance/susceptibility: No observations to date.

I claim:

1. A new and distinct cultivar of geranium plant named 'Fip 765', as described and illustrated herein.

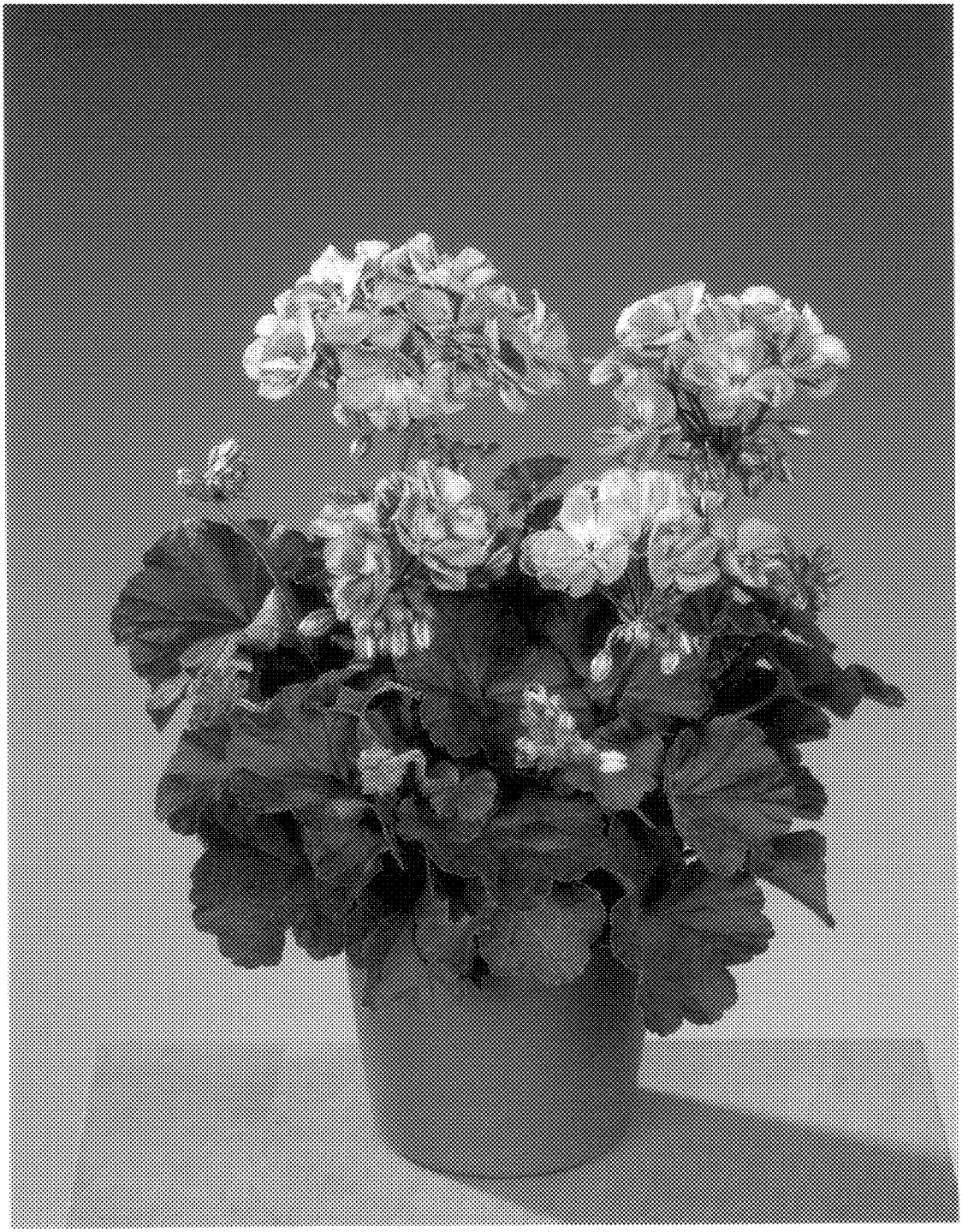

* * * * *